(12) United States Patent
Vrba et al.

(10) Patent No.: US 6,623,504 B2
(45) Date of Patent: *Sep. 23, 2003

(54) BALLOON CATHETER WITH RADIOPAQUE DISTAL TIP

(75) Inventors: Anthony C. Vrba, Maple Grove, MN (US); Jason T. Lenz, Maplewood, MN (US); Steven P. Mertens, Plymouth, MN (US)

(73) Assignee: SciMed Life Systems, Inc., Maple Grove, MN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 67 days.

(21) Appl. No.: 09/733,355

(22) Filed: Dec. 8, 2000

(65) Prior Publication Data
US 2002/0072705 A1 Jun. 13, 2002

(51) Int. Cl.$^7$ .............................................. A61M 29/00
(52) U.S. Cl. ...................................................... 606/192
(58) Field of Search .................. 606/192, 193, 606/194, 198, 195; 623/1.11; 604/96.01

(56) References Cited

U.S. PATENT DOCUMENTS

| | | | |
|---|---|---|---|
| 3,911,927 A | 10/1975 | Rich et al. | 128/349 R |
| 4,085,185 A | 4/1978 | Adair | 264/248 |
| 4,195,637 A | 4/1980 | Grüntzig et al. | 128/348 |
| 4,249,536 A | 2/1981 | Vega | 128/349 B |
| 4,251,305 A | 2/1981 | Becker et al. | 156/86 |
| 4,307,722 A | 12/1981 | Evans | 128/344 |
| 4,323,071 A | 4/1982 | Simpson et al. | 128/343 |
| 4,385,635 A | 5/1983 | Ruiz | 128/658 |
| 4,413,989 A | 11/1983 | Schjeldahl et al. | 604/96 |
| 4,425,919 A | 1/1984 | Alston, Jr. et al. | 128/658 |
| 4,531,512 A | 7/1985 | Wolvek et al. | 128/1 D |
| 4,531,943 A | 7/1985 | Van Tassel et al. | 604/280 |
| 4,540,404 A | 9/1985 | Wolvek | 604/96 |
| 4,551,292 A | 11/1985 | Fletcher et al. | 264/139 |
| 4,571,240 A | 2/1986 | Samson et al. | |
| 4,588,399 A | 5/1986 | Nebergall et al. | 604/280 |
| 4,596,563 A | 6/1986 | Pande | 604/264 |
| 4,636,272 A | 1/1987 | Riggs | 156/158 |

(List continued on next page.)

FOREIGN PATENT DOCUMENTS

| | | |
|---|---|---|
| EP | 0 171 884 A1 | 2/1986 |
| EP | 0 448 886 A1 | 10/1991 |
| EP | 0 452 595 A1 | 10/1991 |
| EP | 0 237 564 B1 | 12/1991 |
| EP | 0 594 201 A2 | 4/1994 |
| EP | 0 688 576 A1 | 12/1995 |
| EP | 0 452 901 B1 | 1/1996 |
| WO | WO 93/17750 | 9/1993 |
| WO | WO 94/01160 | 1/1994 |
| WO | WO 96/38193 | 12/1996 |
| WO | WO 96/39205 | 12/1996 |
| WO | WO 00/45885 | 8/2000 |

OTHER PUBLICATIONS

*Plastics Digest*, Edition 15, vol. 2, 1994, pp. 2–314.

Kohan, *Nylon Plastics Handbook*, Hanser/Gardner Publications, Inc., Cincinnati, Ohio, Copyright 1995, pp. 378–387.

*Primary Examiner*—Kevin T. Truong
(74) *Attorney, Agent, or Firm*—Crompton, Seager & Tufte, LLC

(57) ABSTRACT

A balloon catheter in which its distal tip is precisely positionable in order to control movement of the catheter through tortuous vasculature and especially through the lumen of a deployed stent is disclosed. The distal tip of the catheter is rendered radiopaque, at least at its distal-most end, to enable visualization of the position of the catheter and to facilitate placing the catheter in the desired position.

15 Claims, 2 Drawing Sheets

U.S. PATENT DOCUMENTS

| | | | |
|---|---|---|---|
| 4,636,346 A | 1/1987 | Gold et al. | 264/139 |
| 4,646,719 A | 3/1987 | Neuman et al. | 128/1 D |
| 4,676,229 A | 6/1987 | Krasnicki et al. | 128/4 |
| 4,706,670 A | 11/1987 | Andersen et al. | 128/344 |
| 4,739,768 A | 4/1988 | Engelson | 128/658 |
| 4,748,982 A | 6/1988 | Horzewski et al. | 128/244 |
| 4,753,765 A | 6/1988 | Pande | 264/149 |
| 4,759,748 A | 7/1988 | Reed | 604/95 |
| 4,764,324 A | 8/1988 | Burnham | 264/103 |
| 4,782,834 A | 11/1988 | Maguire et al. | 128/344 |
| 4,808,164 A | 2/1989 | Hess | 604/95 |
| 4,817,613 A | 4/1989 | Jaraczewski et al. | 128/658 |
| 4,819,751 A | 4/1989 | Shimada et al. | 128/344 |
| 4,820,349 A | 4/1989 | Saab | 128/344 |
| 4,863,442 A | 9/1989 | DeMello et al. | 604/282 |
| 4,884,573 A | 12/1989 | Wijay et al. | 128/344 |
| 4,886,506 A | 12/1989 | Lovgren et al. | 604/280 |
| RE33,166 E | 2/1990 | Samson | 606/194 |
| 4,898,896 A | 2/1990 | Maj et al. | 528/323 |
| 4,906,244 A | 3/1990 | Pinchuk et al. | 606/194 |
| 4,917,666 A | 4/1990 | Solar et al. | 604/95 |
| 4,323,071 A | 5/1990 | Simpson et al. | 128/343 |
| 4,921,483 A | 5/1990 | Wijay et al. | 604/96 |
| 4,943,278 A | 7/1990 | Euteneuer et al. | 604/96 |
| 4,950,239 A | 8/1990 | Gahara et al. | |
| 4,955,377 A | 9/1990 | Lennox et al. | 128/401 |
| 4,955,862 A | 9/1990 | Sepetka | 604/164 |
| 4,960,410 A | 10/1990 | Pinchuk | 604/96 |
| 4,964,409 A | 10/1990 | Tremulis | 128/657 |
| 4,964,853 A | 10/1990 | Sugiyama et al. | 604/96 |
| 4,976,720 A | 12/1990 | Machold et al. | 606/194 |
| 4,994,018 A | 2/1991 | Saper | 600/18 |
| 4,994,032 A | 2/1991 | Sugiyama et al. | 604/96 |
| 4,998,923 A | 3/1991 | Samson et al. | 604/194 |
| 5,002,559 A | 3/1991 | Tower | 606/194 |
| 5,047,045 A | 9/1991 | Arney et al. | 606/194 |
| 5,050,606 A | 9/1991 | Termulis | 128/637 |
| 5,078,702 A | 1/1992 | Pomeranz | 604/280 |
| 5,078,727 A | 1/1992 | Hannam et al. | 605/194 |
| 5,093,546 A | 3/1992 | Matsumiya et al. | 219/10.41 |
| 5,100,381 A | 3/1992 | Burns | 604/96 |
| 5,120,308 A | 6/1992 | Hess | 604/95 |
| 5,122,125 A | 6/1992 | Deuss | 604/282 |
| 5,139,496 A | 8/1992 | Hed | 606/23 |
| 5,143,093 A | 9/1992 | Sahota | 128/898 |
| 5,147,377 A | 9/1992 | Sahota | 606/194 |
| 5,154,725 A | 10/1992 | Leopold | 606/194 |
| 5,156,594 A | 10/1992 | Keith | 604/96 |
| 5,156,612 A | 10/1992 | Pinchuk et al. | 606/194 |
| 5,158,548 A | 10/1992 | Lau et al. | 604/96 |
| 5,159,937 A | 11/1992 | Tremulis | 128/772 |
| 5,171,230 A | 12/1992 | Eland et al. | 604/250 |
| 5,176,637 A | 1/1993 | Sagae | 604/96 |
| 5,180,585 A | 1/1993 | Jacobson et al. | 424/405 |
| 5,209,728 A | 5/1993 | Kraus et al. | 604/96 |
| 5,213,574 A | 5/1993 | Tucker | 604/93 |
| 5,221,270 A | 6/1993 | Parker | 604/282 |
| 5,226,888 A | 7/1993 | Arney | 604/96 |
| 5,234,416 A | 8/1993 | Macaulay et al. | 604/282 |
| 5,240,537 A | 8/1993 | Bodicky | 156/244.13 |
| 5,246,420 A * | 9/1993 | Kraus et al. | 606/194 |
| 5,254,091 A | 10/1993 | Aliahmad et al. | 604/96 |
| 5,256,144 A | 10/1993 | Kraus et al. | 604/96 |
| 5,258,160 A | 11/1993 | Utsumi et al. | 264/558 |
| 5,259,839 A | 11/1993 | Burns | 604/99 |
| 5,270,086 A | 12/1993 | Hamlin | 428/35.2 |
| 5,279,561 A | 1/1994 | Roucher et al. | 604/96 |
| 5,279,562 A | 1/1994 | Sirhan et al. | 604/96 |
| 5,304,134 A | 4/1994 | Kraus et al. | 604/96 |
| 5,304,198 A | 4/1994 | Samson | 606/194 |
| 5,316,706 A | 5/1994 | Muni et al. | 264/25 |
| 5,318,032 A | 6/1994 | Lonsbury et al. | 128/658 |
| 5,318,527 A | 6/1994 | Hyde et al. | 604/95 |
| 5,318,532 A | 6/1994 | Frassica | 604/96 |
| 5,324,259 A | 6/1994 | Taylor et al. | 604/96 |
| 5,324,263 A | 6/1994 | Kraus et al. | 604/96 |
| 5,328,468 A | 7/1994 | Kaneko et al. | 604/96 |
| 5,334,148 A | 8/1994 | Martin | 604/96 |
| 5,334,168 A | 8/1994 | Hemmer | 604/281 |
| 5,335,410 A | 8/1994 | Burnham | 29/452 |
| 5,342,386 A | 8/1994 | Trotta | 606/194 |
| 5,344,400 A | 9/1994 | Kaneko et al. | 604/96 |
| 5,346,505 A | 9/1994 | Leopold | 606/194 |
| 5,370,615 A | 12/1994 | Johnson | 604/96 |
| 5,370,655 A | 12/1994 | Burns | 606/194 |
| 5,387,193 A | 2/1995 | Miraki | 604/96 |
| 5,389,087 A | 2/1995 | Miraki | 604/247 |
| 5,397,306 A | 3/1995 | Nobuyoshi et al. | 604/96 |
| 5,399,164 A | 3/1995 | Snoke et al. | 604/95 |
| 5,403,292 A | 4/1995 | Ju | 604/282 |
| 5,405,338 A | 4/1995 | Kranys | 604/282 |
| 5,411,477 A | 5/1995 | Saab | 604/96 |
| 5,423,754 A | 6/1995 | Cornelius et al. | 604/103 |
| 5,425,709 A | 6/1995 | Gambale | 604/96 |
| 5,425,712 A | 6/1995 | Goodin | 604/96 |
| 5,441,484 A * | 8/1995 | Atkinson et al. | 604/96.01 |
| 5,454,795 A | 10/1995 | Samson | 604/282 |
| 5,458,613 A | 10/1995 | Gharibadeh et al. | 606/194 |
| 5,470,322 A | 11/1995 | Horzewski et al. | 604/280 |
| 5,480,383 A | 1/1996 | Bagnoisan et al. | 604/96 |
| 5,496,271 A | 3/1996 | Burton et al. | 604/54 |
| 5,496,294 A | 3/1996 | Hergenrother et al. | 604/282 |
| 5,503,263 A | 4/1996 | Watanabe | 198/442 |
| 5,509,910 A | 4/1996 | Lunn | 604/282 |
| 5,531,715 A | 7/1996 | Engelson et al. | 604/265 |
| 5,538,513 A | 7/1996 | Okajima | 604/282 |
| 5,540,236 A | 7/1996 | Ginn | 128/772 |
| 5,542,924 A | 8/1996 | Snoke et al. | 604/95 |
| 5,542,937 A | 8/1996 | Chee et al. | 604/280 |
| 5,549,552 A | 8/1996 | Peters et al. | 604/96 |
| 5,549,556 A | 8/1996 | Ndondo-Lay et al. | 604/102 |
| 5,554,121 A | 9/1996 | Ainsworth et al. | 604/96 |
| 5,554,139 A | 9/1996 | Okajima | 604/282 |
| 5,569,200 A | 10/1996 | Umeno et al. | 604/96 |
| 5,569,218 A | 10/1996 | Berg | 604/282 |
| 5,605,543 A | 2/1997 | Swanson | 604/96 |
| 5,643,209 A | 7/1997 | Fugoso et al. | 604/96 |
| 5,645,528 A | 7/1997 | Thome | 604/96 |
| 5,649,908 A | 7/1997 | Itoh | 604/96 |
| 5,702,439 A | 12/1997 | Keith et al. | 604/96 |
| 5,716,373 A | 2/1998 | Wolvek et al. | 606/194 |
| 5,725,513 A | 3/1998 | Ju et al. | 604/280 |
| 5,728,063 A | 3/1998 | Preissman et al. | 604/96 |
| 5,743,876 A | 4/1998 | Swanson | 604/96 |
| 5,843,050 A | 12/1998 | Jones et al. | 604/280 |
| 5,891,110 A | 4/1999 | Larson et al. | 604/280 |
| 5,944,712 A | 8/1999 | Frassica et al. | |
| 6,048,338 A | 4/2000 | Larson et al. | 604/523 |

* cited by examiner

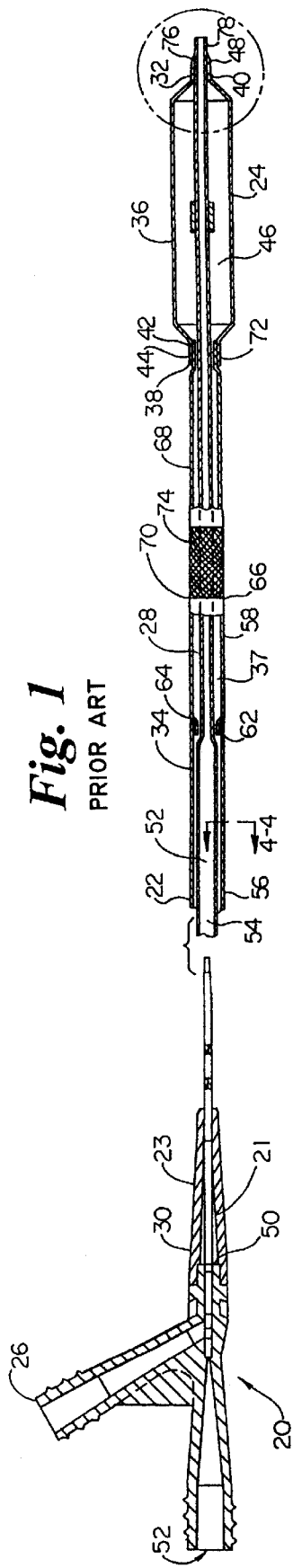
Fig. 1
PRIOR ART
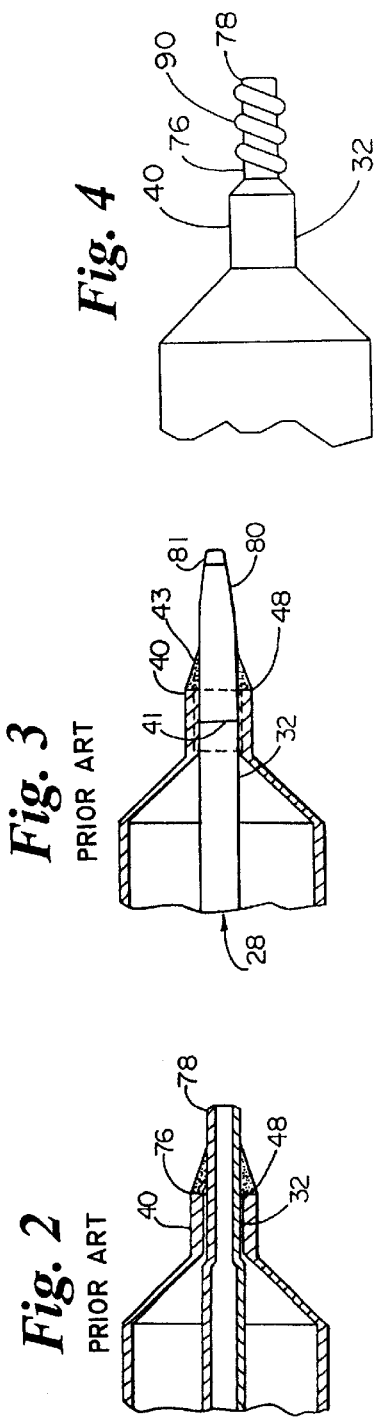
Fig. 2
PRIOR ART
Fig. 3
PRIOR ART
Fig. 4

BALLOON CATHETER WITH RADIOPAQUE DISTAL TIP

TECHNICAL FIELD

This invention relates to the field of intravascular medical devices and more particularly to balloon dilatation and stent delivery catheters which are readily trackable within vasculature in which they are used.

BACKGROUND OF THE INVENTION

Intravascular diseases are commonly treated by relatively non-invasive techniques such as percutaneous transluminal angioplasty (PTA) and percutaneous transluminal coronary angioplasty (PTCA). These therapeutic techniques are well known in the art and typically involve the use of a balloon catheter with a guidewire, possibly in combination with other intravascular devices such as stents. A typical balloon catheter has an elongate shaft with a balloon attached proximate the distal end and a manifold attached to the proximal end. In use, the balloon catheter is advanced over the guidewire such that the balloon is positioned adjacent a restriction in a diseased vessel. The balloon is then inflated and the restriction in the vessel is opened.

There are three basic types of intravascular catheters for use in such procedures, including fixed-wire (FW) catheters, over-the-wire (OTW) catheters and single-operator-exchange (SOE) catheters. The general construction and use of FW, OTW and SOE catheters are all well known in the art. An example of an OTW catheter may be found in commonly assigned U.S. Pat. No. 5,047,045 to Arney et al. An example of an SOE balloon catheter is disclosed in commonly assigned U.S. Pat. No. 5,156,594 to Keith.

Several characteristics that are important in intravascular catheters include pushability, trackability and crossability. Pushability refers to the ability to transmit force from the proximal end of the catheter to the distal end of the catheter. Trackability refers to the ability to navigate tortuous vasculature. Crossability refers to the ability to navigate the balloon catheter across narrow restrictions in the vasculature, such as stenosed vessels or fully and partially deployed stents.

To maximize pushability, some prior art catheters incorporate a stainless steel outer tube (also referred to as a hypotube) on the proximal shaft section and a polymeric distal shaft section. One limitation of such a construction is that hypotubing is often prone to kinking. To reduce the likelihood of kinking, some prior art catheters use a relatively stiff polymer (e.g., composite) or reinforced polymer in the proximal shaft section.

The trackability of a particular catheter design is analyzed in terms of the trackability of the distal portion of the catheter, as this portion must track the guidewire through small tortuous vessels to reach the area to be treated. A more flexible distal portion has been found to improve trackability. Therefore, to maximize pushability, the catheter should have a relatively stiff proximal section. To maximize trackability, the catheter should have a relatively flexible distal section. To maximize crossability, in addition to the characteristics needed for pushability and trackability, the catheter should have a distal tip, the location of which within the vessel can be readily determined so that the progress of the catheter through the vessel can be followed.

One limitation of the basic structure of catheters described above is that kinking can occur at the joint between the relatively stiff proximal shaft section and the relatively flexible distal shaft section. To reduce the likelihood of kinking, some prior art catheters use one or more tubular sections of intermediate flexibility between the relatively stiff proximal section and the relatively flexible distal section to provide a more gradual transition in flexibility therebetween. While this approach provides some benefit, the resulting transition in flexibility is often step-wise, and can still be susceptible to kinking at the junctions of the various intermediate sections. In order to overcome this deficiency, an intravascular catheter that has a more gradual transition in flexibility along its length has been needed. A catheter satisfying this need is described in commonly assigned U.S. Pat. No. 5,891,110 to Larson et al., which is incorporated herein by reference.

However, while overcoming some of the problems with regard to flexibility, comparatively little effort has been directed toward facilitating control of the direction of the catheter tip with respect to a deployed stent or a stenosis. Recrossing a deployed self-expanding or balloon-expandable stent with a post-dilation balloon catheter or additional stent delivery catheter, for example, can prove to be a difficult procedure. Inability of the catheter to cross the stent might be due to failing to direct the distal tip of the catheter into the stent lumen. Instead, the distal tip could be directed into the vessel wall or could get hung up in the struts of the stent. It is also possible for the guidewire to be misdirected by threading it between the stent and the wall of the vessel instead of through the stent lumen. The end result would be that the balloon catheter would get stuck in the vessel and could not be easily removed.

Previous attempts to provide catheters that are more readily visualized within the vessel have involved the utilization of radiopaque markers in catheters. For example, it has been proposed to track the balloon of a balloon catheter by placing radiopaque bands inside the balloon. Such bands, however, are of little assistance in positioning the distal-most end of the catheter tip, which may be separated from the balloon by a distance of several centimeters.

It would be desirable, therefore, to provide a catheter having improved crossability. It would also be desirable to provide a catheter in which the precise position of the distal tip relative to a deployed balloon, stent or stenosis could be readily ascertained.

SUMMARY OF THE INVENTION

The present invention overcomes many of the disadvantages of the prior art by providing a balloon catheter having a distal tip which can be readily located and its position closely followed within vasculature in which it is deployed. The balloon catheter of the present invention is rendered radiopaque proximate the distal-most tip thereof, enabling the physician to observe the position of the tip of the catheter within the body of the patient. Precise placement of the catheter tip by the physician is thereby facilitated.

Radiopacity can be imparted proximate the distal-most tip of the catheter in any of various ways. These include, among others, (1) embedding the catheter tip with radiopaque powder or particles, (2) applying a radiopaque pigment, such as a paint or ink, to the surface of the tip of the catheter, (3) using a radiopaque contrast media to coat the interior surface of a balloon immediately adjacent the distal-most end of the catheter tip, (4) providing bands of radiopaque material proximate the distal-most end of the catheter tip, (5) providing a coil of radiopaque material encircling the distal-most end of the catheter tip, (6) covering at least part of the catheter tip adjacent the distal-most end thereof with a radiopaque mesh or braid, (7) incorporating radiopaque wires in the wall of at least part of the catheter tip adjacent the distal-most end thereof, (8) capping the distal-most end of the catheter tip with a radiopaque cap, and (9) using an arc of a radiopaque hypotube or similar tubing to encircle at least that part of the catheter tip adjacent the distal-most end thereof. Other ways of imparting radiopacity to at least that part of the catheter tip adjacent or proximate the distal-most end thereof are within the scope of the present invention.

Rendering the catheter tip radiopaque proximate its distal-most end is especially important in balloon catheters, because guiding the catheter tip within stenosed vasculature and particularly through stents deployed therein requires knowledge of the precise position of the catheter tip. A radiopaque catheter tip of the present invention can be viewed within body vasculature from outside the body to enable precise maneuvering and placement of the catheter with respect to the stenosed area or to facilitate passage through deployed stents and the like.

BRIEF DESCRIPTION OF THE DRAWINGS

Other objects of the present invention and many of the attendant advantages thereof will be readily appreciated as the same become better understood by reference to the following detailed description when considered in connection with the accompanying drawings, in which like reference numerals designate like parts throughout the figures thereof and wherein:

FIG. 1 is a cross-sectional view of a representative prior art catheter of the type used with the present invention;

FIG. 2 is a partial cross-sectional view of a prior art distal tip area of a catheter as in FIG. 1;

FIG. 3 is a partial cross-sectional view of another prior art design of the distal tip area of the catheter of FIG. 1;

FIG. 4 is a plan view of the distal end of a balloon catheter showing one preferred embodiment of the present invention;

DETAILED DESCRIPTION OF THE INVENTION

Figure 5:
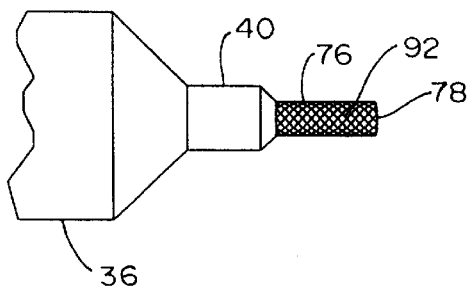
FIG. 5 is a plan view of another preferred embodiment of the present invention.

The following detailed description should be read with reference to the drawings in which like elements in different drawings are numbered identically. The drawings, which are not necessarily to scale, depict selected embodiments and are not intended to limit the scope of the invention.

Examples of constructions, materials, dimensions and manufacturing processes are provided for selected elements. All other elements employ that which is known to those skilled in the field of the invention. Those skilled in the art will recognize that many of the examples provided have suitable alternatives which may also be utilized.

Referring now to the drawings, FIG. 1 is a cross-sectional view of an over-the-wire (OTW) balloon catheter, which is representative of one type of catheter that can incorporate the present invention. Other intravascular catheter embodiments are additionally suitable without deviating from the spirit and scope of the present invention. For example, intravascular catheters suitable for incorporating the present invention include fixed-wire (FW) catheters and single-operator-exchange (SOE) catheters.

The balloon catheter 20 includes a shaft assembly 22 and a balloon assembly 24 connected proximate the distal end of shaft assembly 22. A conventional OTW-type manifold assembly 26 is connected to the proximal end of the shaft assembly 22. The shaft assembly 22 includes an inner tube 28 having a proximal end 30 and a distal end 32. The proximal end of the shaft assembly 21 extends into a manifold assembly 26 adhesively bonded to the shaft assembly 22. A polyurethane strain relief 23 is snap-fit to the manifold assembly 26, and the shaft assembly 22 extends into the manifold assembly 26 through the polyurethane strain relief 23. An outer tube 34 is co-axially disposed about the inner tube 28 to define an annular inflation lumen 37 therebetween.

The balloon assembly 24 includes a balloon body portion 36 with a proximal balloon waist 38 and a distal balloon waist 40. The proximal balloon waist 38 is connected to the outer tube 34 near its distal end 42 by means of an adhesive 44, or alternatively, is thermally bonded. The distal balloon waist 40 is connected to the inner tube 28 near its distal end 32 by means of an adhesive bond 48 or a thermal bond such that the interior of the balloon 46 is in fluid communication with the annular inflation lumen 37.

A radiopaque marker band 50 may be adhesively secured with cyanoacrylate to the inner tube 28 at a point underneath the balloon body 36. Alternatively, the marker band may be swaged onto the outer surface of the inner tube 28 within the balloon.

The inner tube 28 defines a guidewire lumen 54, which provides a passage for a guidewire (not shown). The outer tube 34 defines an annular inflation lumen 37, which is in fluid communication with the interior of the balloon 46.

As previously stated, the catheter of the present invention includes an outer tube 34 which may have multiple segments including a relatively stiff proximal outer section, a mid-shaft section of lesser stiffness, and a tapering distal outer section of the least stiffness. The progressive arrangement of more flexible materials as the catheter proceeds distally provides an optimal level of pushability and trackability to navigate tortuous vasculature. The flexibility of the sections of the outer tubular member were tested utilizing a Gurley bending resistance tester, Part No. 4171-DT, as manufactured by Precision Instruments, Troy, N.Y. The apparatus consists of a balanced pendulum or pointer which is center-pivoted and can be weighted at three points below its center. The pointer moves freely in both the left and right directions. A sample of specific size is attached to a clamp, which in turn is located in one of several positions on a motorized arm which also moves left and right. During the test, the sample is moved against the top edge of the vane, moving the pendulum until a sample bends and releases it. The test is run in two steps, first to the left and then to the right. The scale reading is measured in each direction and the results are averaged. The instrument provides a relative flexibility measurement between the components of the outer tubular member as detailed below to achieve improved trackability and pushability.

The outer tube 34 has a relatively stiff, proximal outer section 56 with a proximal end 60 and a distal end 62. The proximal outer tube may be made of nylon, a polyamide, such as DURETHAN available from Bayer, GRILAMID available from EMS-American Grilon, Inc., a DURETHAN, GRILAMID, CRISTAMID or CRISTAMID/VESTAMID blend braid or polyetheretherketone (PEEK) braid. The preferred embodiment of PEEK braid is a variable PIC tube, wherein said PIC varies from about 30 to 100 PIC to give varying flexibility over the length of the proximal outer tube. The PIC preferably varies from about 50 to about 80. The braiding material in the PEEK or DURETHAN (polymer) braid may be made from stainless steel, or Nitinol (nickel titanium alloy). This proximal outer section 56 will have an outside diameter ranging from 0.040 inches to 0.065 inches with a wall thickness ranging from 0.0026 inches to 0.0056 inches. The proximal outer section has a preferred Gurley value of about 700 to about 1300 over its length. A preferred range is about 800 to about 1200.

A midshaft section 58 with a proximal end 64 and a distal end 66 extends distally from the distal end 62 of the proximal outer section 56. The midshaft section 58 has a stiffness less than that of the proximal outer section 56. The midshaft section 58 is preferably made from a polyamide, such as CRISTAMID available from Elf Atochem, having a durometer of about 81D. A preferred Gurley value for the midsection is about 350 to about 500, with a range of 400 to 450 preferred. This midshaft section 58 will have an outside diameter ranging from 0.040 inches to 0.045 inches with a wall thickness ranging from 0.0028 inches to 0.0044 inches.

The distal end of the proximal outer section 62 is joined to the proximal end of the midshaft section 64 with a urethane adhesive bond or a thermal weld. A distal outer section 68 having a proximal end 70 and a distal end 72 extends distally from the distal end of the midshaft section 66 to the distal end of the outer tube 44. This distal outer section 68 is more flexible or has less stiffness than both the proximal outer section 56 and the midshaft section 58. The outer diameter of the distal outer section 68 will taper from about 0.045 inches at the proximal end 70 to 0.030 inches at the distal end 72. This distal outer section 68 is made of polyether block amide (PEBAX) with a durometer of 70D. The tapered distal outer section preferably has a Gurley value of about 70 to about 90 at its proximal end and about 15 to about 40 at its distal end. Thus, the distal end of the distal outer section 72 will exhibit less stiffness than the proximal end of the distal outer section 70. The distal end of the midshaft section 66 is joined to the proximal end of the distal outer section 70 with a urethane adhesive bond or a thermal weld.

A Nitinol braid insert 74 with a length of about 1.0 inches is placed within the proximal end of the distal outer section 70 to provide strain relief and reduce kinkability at the midshaft/distal outer section junction. This Nitinol braid 74 has a 0.001 inches×0.005 inches ribbon.

The inner tube 28 is made of polyethylene such as Marlex HDPE or a multilayer co-extrusion with Marlex interior layer and PEBAX outer layer. At the proximal end of the inner tube 30, the inner tube 28 has an outside diameter ranging from 0.022 inches to 0.028 inches and preferably about 0.025 inches, with the inner tube 28 having an inside diameter ranging from 0.016 inches to 0.021 inches for a 0.014 inch guidewire with which this lumen is designed to be compatible. The inner tube 28 has a wall thickness ranging from 0.0024 inches to 0.005 inches and preferably about 0.0032 inches. The outside diameter-to-wall thickness ratio must be sufficiently small to minimize the propensity of kinking.

As the inner tube 28 extends distally through the junction area between the distal end of the proximal outer section 62 and the proximal end of the midshaft section 64 of the outer tube 28, both the inner and outer diameters of the inner tube 28 will taper from wider diameters to narrower diameters. Likewise, at the distal end of the inner tube 32, both the inner and outer diameters of the inner tube 28 will once again taper from wider diameters to narrower diameters as the tube extends distally.

As illustrated in FIG. 2, which shows details of the catheter assembly of FIG. 1, a distal tip 76 having a distal-most end 78 is formed on the distal end of the inner tube 32, where the inner tube 28 distally tapers from a larger outer diameter to a smaller outer diameter. The distal balloon waist 40 is attached to the distal tip 76 through a urethane adhesive bond or thermal bond at a bonding area. The area just distal of the distal waist bond is backfilled with adhesive 43 to provide a smooth transition. The adhesive coating provides for improved adhesion between dissimilar substrates.

The proximal catheter shaft portion is preferably about 35 to 45 inches in length with a preferred length of 42 inches. The midshaft section, if included, can be about 1 to about 3 inches in length with a preferred length of 2 inches. The distal outer section having the most flexibility is preferably about 8 to about 12 inches in length with a preferred length of about 10 inches.

In another embodiment of the catheter assembly of FIG. 1, as shown in FIG. 3, a polyethylene, polyamide, or block copolymer such as PEBAX distal tip 80 having a durometer between about 50D and 70D, preferably about 63D is heat welded or bonded to the distal end of the inner tube 32 with a durometer of about 63–65D, and the distal balloon waist 40 of the balloon is adhesively or thermally bonded to both the inner tube and the tip extending therefrom. As shown in FIG. 3, the joint 41 between the inner tube and the tip is located under the distal waist of the balloon. The outer diameter of the polyethylene distal tip 80 distally tapers from a larger outer diameter to a smaller outer diameter.

In another embodiment also shown in FIG. 3, the last ½ to 1 mm of the tip at its distal end is made of a different material from the tip material to form a tip extension. In particular, the last ½ to 1 mm is made from a material which is more durable relative to the softer tip material. In particular, the more durable material will resist deforming or tearing when in use, such as in tracking tortuous anatomy or in moving through a deployed stent. For example, this last ½ mm to 1 mm may be manufactured from Marlex high-density polyethylene having a 63D durometer which improves the integrity of the tip portion at its distal-most end 81.

FIG. 4 shows a preferred embodiment of a tip assembly which can be included in catheters such as that in FIGS. 1 and 3. In the embodiment, radiopacity is provided to the tip assembly proximate its distal-most end by a radiopaque coil. Distal tip 76 is positioned distally from the distal balloon waist 40 of balloon 36. In particular, the distal tip is illustrated as having a coil 90 encircling the distal-most end 78. Coil 90 may be comprised of any radiopaque material. Preferable materials forming coil 90 include any metals or plastics being radiopaque, or capable of being impregnated with radiopaque materials. In particular, tungsten, tantalum, platinum, gold, and the like are examples of preferred materials forming coil 90.

Coil 90 is preferably wire-shaped. Various shaped wires, however, may be used to form coil 90. As such, coil 90 may be manufactured as a round wire, a wire ribbon, a cable wire, or a machined hypotube. The wire is wound about the distal tip 76, imparting a helical configuration to coil 90. Coil 90 may additionally encircle distal tip 76 through a series of connected spirals or concentric rings. In preferred embodiments, the windings of coil 90 terminate prior to reaching the distal-most end 78 of distal tip 76.

The longitudinal spacing and tensile strength of the windings may vary from catheter to catheter. By varying the longitudinal spacing and tensile strength, the physical characteristics of the distal tip 76 may be altered. For example, close spacing and elevated tensile strength often result in an increase in the stiffness of the distal tip 76, and more particularly, causing the distal-most end 78 to become less supple. Larger spacing and lower tensile strength, on the other hand, while still decreasing the flexibility of the distal tip 76 alone, retain a sufficiently supple distal-most end 78.

FIG. 5 shows another preferred embodiment of a tip assembly in which radiopacity is contributed by a radiopaque mesh material. A radiopaque mesh 92 extends generally from distal balloon waist 40 of balloon 36 proximate distal-most end 78 of distal tip 76. Depending upon the flexibility desired for the catheter tip, the mesh can either encircle distal tip 76 entirely, or only a portion thereof. Alternatively, distal tip 76 can itself be fabricated of the radiopaque mesh material 92.

When radiopaque mesh 92 is attached to the distal tip 76, the attachment generally occurs through the use of a urethane adhesive or thermal bond at the desired bonding location. A thermal bond permits embedding the radiopaque mesh 92 into the surrounding polymeric material forming distal tip 76. Embedding the mesh affords a manufacturer the option of eliminating the need to backfill the area just distal of the distal balloon waist 40. The embedding procedure itself provides a smooth transition along the distal tip 76. Backfilling, when desired, is generally accomplished using an adhesive or other suitable polymeric material. Backfilling may additionally occur toward the distal-most end 78, or over the radiopaque mesh 92, to insure a smooth transition throughout the distal tip 76.

In an alternative embodiment, a radiopaque braid can be used in place of the radiopaque mesh material. A further embodiment provides that a polymeric material may be extruded over the radiopaque mesh or braid 92 forming a distal tip 76 having a lumen 54 extending longitudinally therein.

Figure 6A:
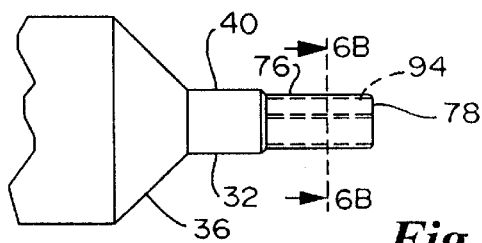
FIG. 6A is a plan view of another preferred embodiment of the present invention.
Figure 6B:
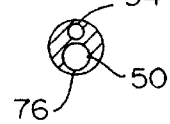
FIG. 6B is a cross-section of the embodiment of FIG. 6A along the line 6B—6B.

FIGS. 6A and 6B show another preferred embodiment of a tip assembly in which the radiopacity is provided by a radiopaque member or wire incorporated into the wall of the catheter tip. A radiopaque wire 94, shown in phantom in FIG. 6A, is embedded in distal tip 76. Various shaped wires may be used to form wire 94. As such, radiopaque wire 94 may be manufactured as a round wire, a wire ribbon, a cable wire, or a machined hypotube. Radiopaque wire 94 may be comprised of any radiopaque material. Materials forming radiopaque wire 94 include any metals or plastics being radiopaque or capable of being impregnated with radiopaque materials. In particular, tungsten, tantalum, platinum, gold, and the like, are examples of preferred materials forming radiopaque wire 94.

Radiopaque wire 94 may originate anywhere within balloon distal waist 40 and extend longitudinally until terminating at or proximate the distal-most end 78 of distal tip 76. Preferably, radiopaque wire 94 generally extends longitudinally from the proximal-most end of distal tip 76 and terminates prior to the distal-most end 78 thereof. The radiopaque wire 94 is preferably straight, however, the wire may additionally assume alternative configurations that follow a general longitudinal progression (e.g., a sinusoidal curve).

FIG. 6B shows a cross-section of the distal tip of FIG. 6A having radiopaque wire 94 embedded therein. Lumen 50 is defined by an inner diameter and an outer diameter at the distal tip 76. The inner diameter defines a pathway for the passage of a guidewire. The outer diameter defines the surface of distal tip 76. Radiopaque wire 94 is positioned between the inner and outer diameters. Preferably, radiopaque wire 94 is entirely encapsulated between the inner and outer diameter.

Figure 7:
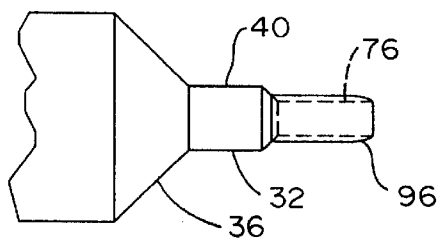
FIG. 7 is a plan view of another preferred embodiment of the present invention.

FIG. 7 shows a radiopaque cap over the distal tip of the catheter. A radiopaque cap 96 surrounds distal tip 76, shown in phantom. Radiopaque cap 96 may be comprised of any radiopaque material. Materials forming radiopaque cap 96 include any metals or plastics being radiopaque or capable of being impregnated with radiopaque materials. In a preferred embodiment, radiopaque cap 96 is made of a high durometer polymeric material. Radiopaque caps of high durometer allow the distal tip region to remain supple, minimizing trauma associated with the catheter's advancement through the surrounding vessel walls.

Since radiopaque cap 96 is formed independent from distal tip 76, the cap may be molded to redefine the original shape of the distal tip 76 of a catheter. For instance, radiopaque cap 96 may form a gradually decreasing taper from where cap 96 seats against balloon waist 40 to the cap's distal-most end. This cap configuration allows for a smooth transition between the distal tip region to the balloon region of a catheter. Alternatively, cap 96 may mimic the shape of a typical distal tip 76 having a straight tubular shape, as illustrated in FIG. 7. Once the cap design is chosen and slid over the distal tip 76, the radiopaque cap 96 is preferably attached to distal tip 76 through a urethane adhesive or by thermal bonding.

Figure 8A:
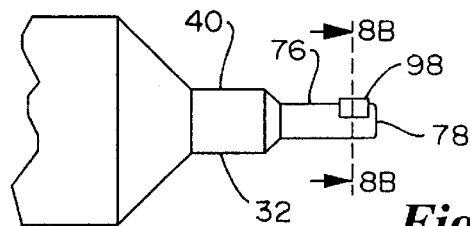
FIG. 8A is a plan view of another preferred embodiment of the present invention.

FIG. 8A shows a half arc hypotube providing radiopacity to the distal-most end of the distal tip. Half arc hypotube 98 is securely attached to distal tip 76. The hypotube 98 may be attached anywhere along the length of distal tip 76. To aid a physician in pinpointing the distal-most end of the catheter, however, it is believed that the hypotube should be placed close to the distal-most end 78 of distal tip 76. Once positioned, hypotube 98 is attached to the outer diameter of the distal tip 76 through a urethane adhesive or by thermal bonding.

Thermal bonding hypotube 98 to distal tip 76 permits the embedding of hypotube 98 into the polymeric material forming distal tip 76. The depth of the subsequent embedding may be varied. In one embodiment, hypotube 98 is embedded into distal tip 76 until the outer diameter of hypotube 98 is flush with the outer diameter of distal tip 76. Alternatively, hypotube 98 may be partially embedded into the polymeric material forming distal tip 76. If desired, backfill of polymeric material may be added to smooth the transition around the exposed portions of hypotube 98.

Figure 8B:
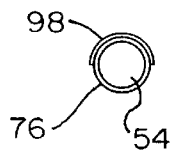
FIG. 8B is a cross-section of the embodiment of FIG. 8A along the line 8B—8B.

FIG. 8B shows a cross-section of the distal tip 76 of FIG. 8A having half arc hypotube 98 attached thereto. Lumen 54 is defined by an inner diameter and an outer diameter. The inner diameter defines a pathway for the passage of a guidewire. The outer diameter defines the outer surface of distal tip 76. As illustrated in FIG. 8B, hypotube 98 is attached directly upon the outer surface of distal tip 76. With this configuration, the edges of half arc hypotube 98 are exposed. Exposed edges may cause trauma to the surrounding vessel walls as the catheter is advanced. To alleviate this possibility for trauma, polymeric material may be added along these exposed edges to smooth the profile of distal tip 76.

Figure 9:
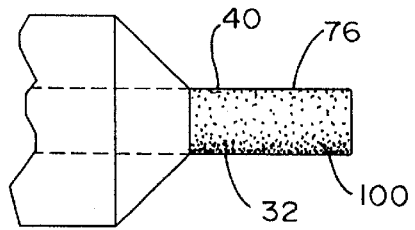
FIG. 9 is a plan view of another preferred embodiment of the present invention.

FIG. 9 shows the distal tip embedded with radiopaque particles. Distal tip 76 is fabricated using a polymeric material impregnated with radiopaque particles 100. Radiopaque particles 100 may be in powder or particulate form. Any radiopaque material may be used that may be readily blended and extruded. Radiopaque particles 100 are preferably blended with a polymeric material capable of forming a soft distal tip 76. The blended material is then extruded to form an elongate distal tip 76 having a lumen 54 extending longitudinally therein. The resultant distal tip 76 may be either extruded simultaneously with the portions of the lumen forming the guidewire lumen, or the extruded distal tip 76 may be attached to the body of the catheter at a later time. If distal tip 76 is extruded independent of the main body of the catheter, the later attachment is preferably accomplished through a urethane adhesive or by thermal bonding. The distal tip may be assembled as described with reference to FIG. 3.

Figure 10:
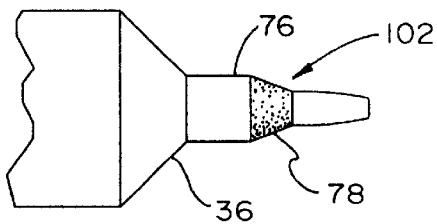
FIG. 10 is a plan view of another preferred embodiment of the present invention.

FIG. 10 shows the use of a radiopaque pigment which is painted upon the distal tip. Radiopaque pigment 102 painted upon the distal tip allows identification of relevant portions on the catheter's body while within a vasculature. In particular, radiopaque pigment may be applied anywhere between the distal-most end 78 and balloon waist 40 of distal tip 76.

Physicians may easily navigate and align a catheter across a stenosis or a stent when the physician accurately knows the location of the catheter's distal-most end 78. Additionally, when radiopaque pigment is applied to balloon waist 40, a physician may easily align the balloon within a stent. When a balloon is accurately positioned within a stent, on expansion, the stent opens with uniformity and with reduced trauma to the surrounding vasculature.

In an alternative embodiment, radiopaque pigment 102 may be incorporated into a polymeric backfill. Backfill having radiopaque pigment 102 may be added to portions of distal tip 76. In particular, backfill may be added upon distal-most end 78 to readily identify the terminal point of the catheter.

Figure 11:
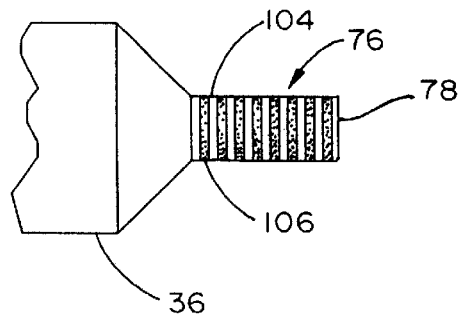
FIG. 11 is a plan view of another preferred embodiment of the present invention.

FIG. 11 shows alternating bands of radiopaque material 104 incorporated within distal tip 76. Alternating hard radiopaque material with softer non-radiopaque material is possible. Bands 104 of radiopaque material may also alternate with bands 106 of non-radiopaque material throughout the length of distal tip 76. In an alternative embodiment, the radiopaque material is soft and the non-radiopaque material is hard. The alternating band configuration may additionally be applied to only a portion of distal tip 76, preferably, to the distal-most end.

Alternating bands of different durometers affects the flexibility of distal tip 76. This embodiment provides a more flexible and supple distal tip 76. During catheter advancement, this distal tip design permits aggressive navigation without traumatizing the surrounding vasculature.

In a preferred embodiment, distal tip 76 is comprised wholly of a soft non-radiopaque material. Bands of material are then removed from the distal tip through an abrasion process. Specifically, the band of material is removed by bringing distal tip 76 into contact with a grinding wheel. The distal tip 76 is then rotated 360 degrees to remove the material circumferentially around the tip. The grinding wheel is slowly advanced to increase the depth of the cut. Although abrasion is the preferred method of processing, the band can be created using many different processes, some of which include alternate extrusion methods, cutting, and thermal processing. Material differing in durometer and radiopacity than the one removed from distal tip 76 is then backfilled into the exposed bands. Therefore, backfill material comprising of a hard radiopaque material is filled into the exposed bands of the soft non-radiopaque distal tip 76.

Figure 12:
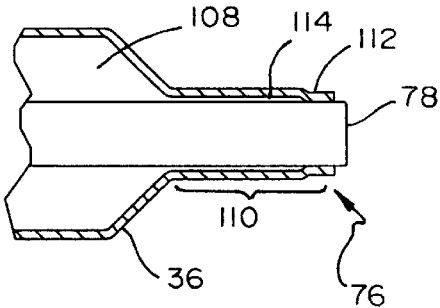
FIG. 12 is a partial cross-sectional view of another preferred embodiment of the present invention.

As illustrated in FIG. 12, the distal region of the catheter includes a balloon with a distal balloon waist 110 connected to the inner tube near its distal-most end. In preferred embodiments, the distal-most end of the distal balloon waist 112 is connected to the inner tube by means of an adhesive bond or thermal bond. Adhesive or thermal bonding permits the interior of the balloon 36 to be in fluid communication with an annular inflation lumen. The distal balloon waist 110 extends proximally from the distal-most end along and slightly above the inner tube forming a narrow channel 114. The proximal end of the narrow channel 114 extends outwardly forming the distal end of balloon 36. As a result, the narrow channel 114 remains in fluid communication with balloon 36. In a preferred embodiment, the portion of distal balloon waist 110 forming the narrow channel 114 comprises a non-compliant balloon material.

A reservoir of contrast media 108 is fluidly connected to balloon 36. The reservoir may dispense contrasting media 108 to balloon 36 when balloon 36 is either in an inflated or deflated state. When balloon 36 is supplied with contrasting media 108, the contrasting media 108 fills both the balloon 36 and the narrow channel 114 under the distal balloon waist 110. Visualization of the distal-most end of the narrow channel 114 is generally a close approximation of the distal-most end 78 of distal tip 76. A physician, therefore, may accurately identify the catheter's positioning within the vasculature by adjusting for the known discrepancy between the distal-most end of the narrow channel 114 and the distal-most end 78 of distal tip 76.

Having thus described the preferred embodiments of the present invention, those of skill in the art will readily appreciate that yet other embodiments may be made and used within the scope of the claims hereto attached.

What is claimed is:

1. In a catheter having a distal portion including an expandable member having a distal end, the expandable member further having a distal waist portion disposed adjacent the distal end of the expandable member, the distal waist portion having an outside diameter and being affixed to a tubular member which extends through at least a portion of the expandable member and beyond the distal end of the expandable member to form a tip portion, the improvement comprising:

a radiopaque means extending along at least a portion of the tip portion of so that in use the radiopaque means renders at least a portion of said tip portion visible under fluoroscopy and the radiopaque means defines an outside diameter of the tip portion that is reduced relative to the outside diameter of the distal waist portion.

2. The improvement of claim 1, wherein the tubular member is a single elongate tube extending through the expandable member and forming the tip.

3. The improvement of claim 1, wherein the tubular member is comprised of multiple tubular segments joined together and a distal tubular segment forms the tip portion.

4. The improvement of claim 3, wherein the expandable member includes a distal waist and the distal tubular segment extends through at least a portion of the distal waist.

5. The improvement of claim 1, wherein the radiopaque means comprises a radiopaque material encircling at least a part of the tip portion.

6. The improvement of claim 1, wherein the radiopaque means comprises a radiopaque material overlying at least a part of the distal tip portion.

7. The improvement of claim 1, wherein the radiopaque means comprises a radiopaque material formed into a coil and secured around at least part of the distal tip portion.

8. A balloon catheter assembly, comprising:
    an outer tube having a proximal end and a distal end with a lumen extending therethrough;
    an elongate inner tube having a proximal end and a distal end with a lumen extending therethrough, said inner tube coaxially disposed within the lumen of the outer tube to form an inflation lumen therebetween; and,
    an inflatable balloon having a proximal waist sealably connected proximate the distal end of the outer tube, and a distal waist sealably connected proximate the distal end of the inner tube, the distal waist having an outside diameter, the interior of the balloon being in fluid communication with the inflation lumen, wherein said inner tube extends distally beyond the distal waist of said balloon to form a tip portion, said tip portion including radiopaque means, said radiopaque means defining an outside diameter for the tip portion that is reduced relative to the outside diameter of the distal waist.

9. The balloon catheter assembly of claim 8, wherein the inner tubular member is a single elongate tube extending through the inflatable balloon and forming the tip portion.

10. The balloon catheter assembly of claim 8, wherein the inner tubular member is comprised of multiple segments joined together and a distal tubular segment of said inner tubular member forms the tip portion.

11. The balloon catheter assembly of claim 10, wherein the expandable member includes a distal waist and the distal tubular segment extends through at least a portion of the distal waist.

12. The balloon catheter assembly of claim 8, wherein the radiopaque means comprises a radiopaque material encircling at least a part of the tip portion.

13. The balloon catheter assembly of claim 8, wherein the radiopaque means comprises a radiopaque material overlying at least a part of the tip portion.

14. The balloon catheter assembly of claim 8, wherein the radiopaque means comprises a radiopaque material formed into a coil and secured around at least part of the tip portion.

15. A balloon catheter comprising:
    an elongate outer tube having a lumen extending the length therein;
    an elongate inner tube coaxially disposed within at least a portion of the elongate outer tube with a distal segment extending distally beyond a distal end of the elongate outer tube, the distal segment including a radiopaque member defining an outside diameter of the distal segment; and
    an inflatable balloon having a proximal waist, a distal waist and an expandable region therebetween, wherein the distal waist of the balloon is sealably connected to the distal segment of the elongate inner tube and wherein the distal waist has an outside diameter that is larger than the outside diameter of the distal segment, and the proximal waist of the inflatable balloon is sealably connected to the elongate outer tube, and further wherein the expandable region of the balloon is in fluid communication with the lumen of the elongate outer tube.

* * * * *